(12) United States Patent
Miwa et al.

(10) Patent No.: US 8,190,231 B2
(45) Date of Patent: May 29, 2012

(54) LYMPH NODE DETECTING APPARATUS

(75) Inventors: Mitsuharu Miwa, Hamamatsu (JP);
Takahiro Shikayama, Hamamatsu (JP);
Toshiyuki Kitai, Yamato Kouriyama (JP)

(73) Assignee: Hamamatsu Photonics K.K.,
Hamamatsu-shi, Shizuoka (JP)

( * ) Notice: Subject to any disclaimer, the term of this patent is extended or adjusted under 35 U.S.C. 154(b) by 382 days.

(21) Appl. No.: 10/580,007

(22) PCT Filed: Nov. 16, 2004

(86) PCT No.: PCT/JP2004/017014
§ 371 (c)(1),
(2), (4) Date: May 2, 2007

(87) PCT Pub. No.: WO2005/048826
PCT Pub. Date: Jun. 2, 2005

(65) Prior Publication Data
US 2007/0276230 A1 Nov. 29, 2007

(30) Foreign Application Priority Data
Nov. 20, 2003 (JP) .................. 2003-391154

(51) Int. Cl.
*A61B 5/05* (2006.01)
(52) U.S. Cl. ......... 600/410; 600/476; 600/473; 600/478
(58) Field of Classification Search .............. 600/410, 600/476, 477, 478, 475
See application file for complete search history.

(56) References Cited

U.S. PATENT DOCUMENTS

| | | | |
|---|---|---|---|
| 4,821,117 A * | 4/1989 | Sekiguchi | 348/68 |
| 5,111,821 A | 5/1992 | Potter | |
| 5,647,368 A | 7/1997 | Zeng et al. | |
| 5,697,885 A * | 12/1997 | Konomura et al. | 600/109 |
| 5,801,763 A | 9/1998 | Suzuki | |
| 6,122,042 A | 9/2000 | Wunderman et al. | |
| 6,510,338 B1 | 1/2003 | Irion et al. | |
| 6,631,286 B2 | 10/2003 | Pfeiffer et al. | |
| 6,915,154 B1 | 7/2005 | Docherty et al. | |
| 2002/0013531 A1* | 1/2002 | Hayashi | 600/476 |
| 2002/0038074 A1 | 3/2002 | Hakamata | |
| 2002/0138008 A1 | 9/2002 | Tsujita et al. | |
| 2002/0196337 A1 | 12/2002 | Takeyama | |

(Continued)

FOREIGN PATENT DOCUMENTS

DE 198 04 797 8/1999

(Continued)

*Primary Examiner* — Tse Chen
*Assistant Examiner* — Joel F Brutus
(74) *Attorney, Agent, or Firm* — Drinker Biddle & Reath LLP

(57) ABSTRACT

A sentinel lymph node detecting apparatus 1 includes: an excitation light source unit 2 that illuminates an excitation light 10 onto a living body observation portion 20 including a sentinel lymph node 21 near a tumor into which a fluorescent dye that emits fluorescence is injected; an optical filter 3 that transmits a fluorescence image 11; an image pickup device 4 that is integral with excitation light source unit 2 and picks up fluorescence image 11 transmitted through optical filter 3; an adjusting device 5 that adjusts the picked-up observation image; and an image displaying device 6 that displays the adjusted observation image. Adjusting device 5 adjusts at least one of a luminance and a contrast of the observation image. A lymph node detecting apparatus that is simple in apparatus arrangement, is easy to handle, and enables good images to be obtained is thereby realized.

7 Claims, 8 Drawing Sheets

U.S. PATENT DOCUMENTS

| | | |
|---|---|---|
| 2003/0120129 A1 | 6/2003 | Nakamura |
| 2003/0187319 A1 | 10/2003 | Kaneko et al. |
| 2004/0109231 A1 | 6/2004 | Haisch et al. |
| 2008/0097198 A1 | 4/2008 | Miwa et al. |

FOREIGN PATENT DOCUMENTS

| | | |
|---|---|---|
| JP | 9-154812 | 6/1997 |
| JP | 2810715 | 7/1998 |
| JP | 2000-292353 | 10/2000 |
| JP | 2000-300509 | 10/2000 |
| JP | 2000-354583 | 12/2000 |
| JP | 2001-78205 | 3/2001 |
| JP | 2001-212070 | 8/2001 |
| JP | 2001-299676 | 10/2001 |
| JP | 2002-95663 | 4/2002 |
| JP | 2002-291682 | 10/2002 |
| JP | 2002-336196 | 11/2002 |
| JP | 3394447 | 1/2003 |
| JP | 2003-66145 | 3/2003 |
| JP | 2003-79570 | 3/2003 |
| JP | 2003-190103 | 7/2003 |
| JP | 2003-215469 | 7/2003 |
| JP | 2004-89236 | 3/2004 |
| JP | 2004-305382 | 11/2004 |
| WO | WO 01/22870 | 4/2001 |
| WO | WO 01/97902 | 12/2001 |
| WO | WO 03/077741 | 9/2003 |
| WO | WO 2004/006816 | 1/2004 |

* cited by examiner

Fig.4
(a) 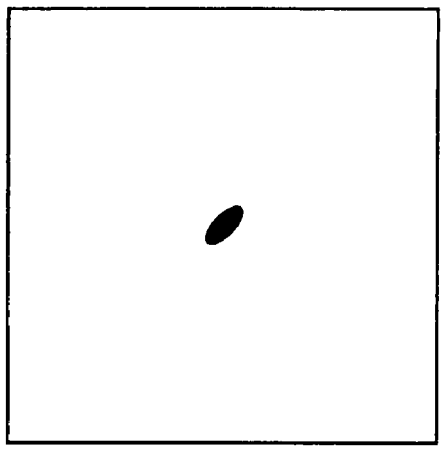
(b) 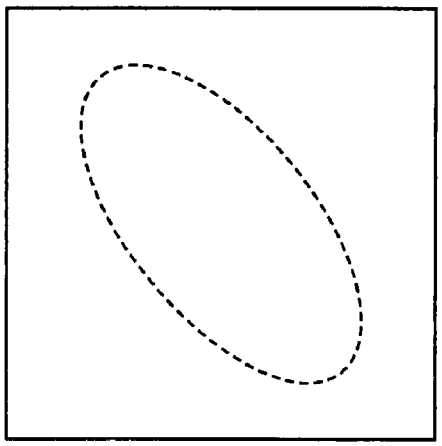
(c) 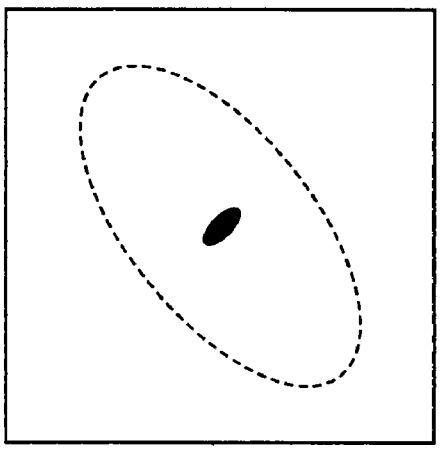

Fig.6
(a)
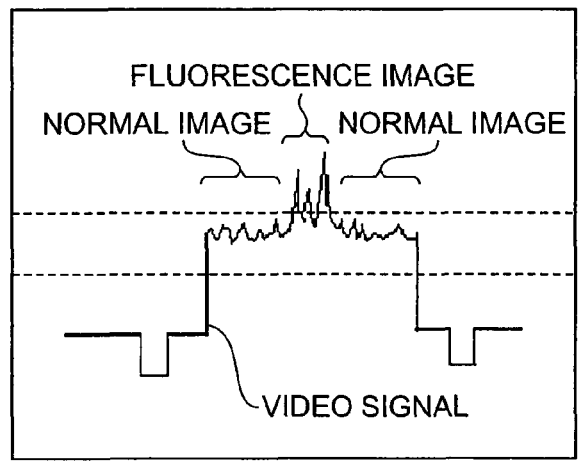
(b)
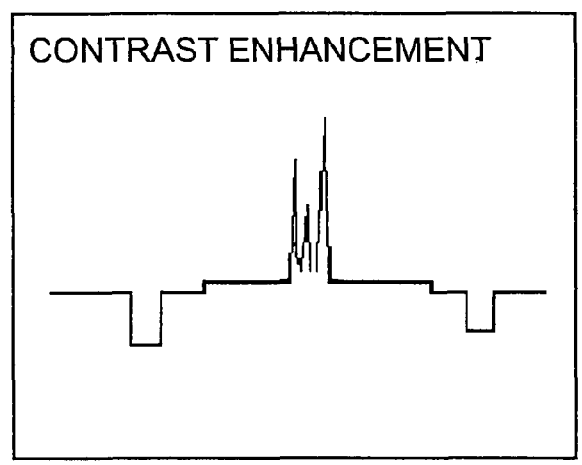
(c)
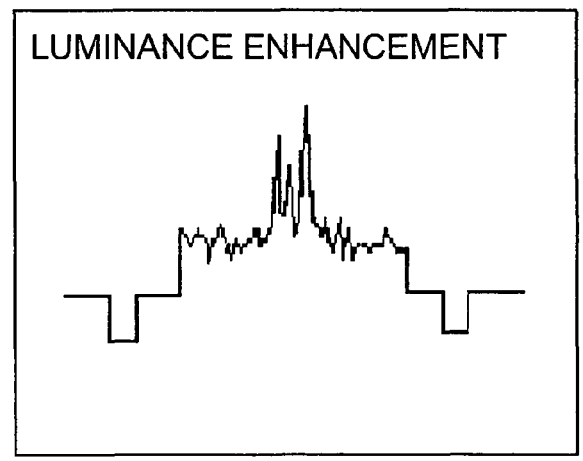

Fig.7
(a)
(b)

LYMPH NODE DETECTING APPARATUS

TECHNICAL FIELD

This invention relates to a lymph node detecting apparatus for detecting a sentinel lymph node or other lymph node by use of a fluorescence image generated by a fluorescent dye.

BACKGROUND ART

A sentinel lymph node is a lymph node that is first reached by cancer cells from a tumor via lymph flow and is the lymph node with the highest possibility of metastasis by the cancer cells. Thus, if the sentinel lymph node is identified correctly and if metastasis by cancer cells is not found therein, it can be considered that there is no metastasis to other organs. Significant reductions in physical and psychological burdens placed on a patient, restraining of treatment costs by omission of ablative surgery, etc., are thus anticipated.

As methods of detecting the sentinel lymph node, dye methods and RI (radioisotope) methods are mainly known. With a dye method, for example, a blue dye, such as indigo carmine, is injected close to a tumor, the lymphatic duct that is dyed in blue is traced visually, and the lymph node that is reached first is detected as the sentinel lymph node. With the RI method, for example, a radioisotope that serves as a tracer is injected close to a tumor, a living body observation portion that is presumed to include the lymph node, at which the radioisotope first arrives and accumulates, is probed from above the skin by a gamma probe, and the living body observation portion at which gamma rays are sensed is detected as the sentinel lymph node.

Methods of identifying a sentinel lymph node using a fluorescent dye have also been proposed. With the sentinel lymph node detecting apparatus disclosed in Patent Document 1, a fluorescent dye is injected close to a tumor in advance, and light of a predetermined wavelength is illuminated as excitation light onto a living body observation portion that is presumed to include the sentinel lymph node in the periphery of the tumor. Identification of the sentinel lymph node is then carried out by converting and displaying a fluorescence image of the near-infrared wavelength band that is generated from the living body observation portion, to and as a visible image.
Patent Document 1: Japanese Patent Application Laid-Open No. 2001-299676

DISCLOSURE OF THE INVENTION

Problems to be Solved by the Invention

However, with the above-described conventional dye method, abundant experience is required to visually trace the lymphatic duct that is dyed in blue, and once the position of the sentinel lymph node is lost track of, the dyeing must be repeated.

With the above-described conventional RI method, though the above-mentioned experience for visually tracing a lymphatic duct and repeating of dyeing are not required, there are such issues as the danger of exposing the surroundings to radiation due to use of a radionuclide, radioisotopes being expensive, etc.

With the above-described conventional sentinel lymph node detecting apparatus that uses a fluorescent dye, though there is no danger of exposure to radiation, the apparatus arrangement is complicated and difficult to handle in medical situations, and good images cannot be obtained necessarily.

The present invention has been made to resolve the above issues and an object thereof is to provide a lymph node detecting apparatus that is simple in apparatus arrangement, is easy to handle, and enables good images to be obtained.

Means for Solving the Problem

In order to achieve the above object, this invention provides a lymph node detecting apparatus that includes: an excitation light source, illuminating excitation light onto a living body observation portion that includes a lymph node near a tumor into which a fluorescent dye that emits fluorescence of a predetermined wavelength has been injected in advance; an optical filter, transmitting a fluorescence image generated from the living body observation portion; an image pickup means for picking up the fluorescence image transmitted through the optical filter; an adjusting means for adjusting at least one of a luminance and a contrast of an observation image output from the image pickup means; and an image displaying means for displaying the observation image, adjusted by the adjusting means, as an image for detecting the lymph node.

By arranging the above-described lymph node detecting apparatus to have the adjusting means that adjusts at least one of the luminance and the contrast of the observation image output from the image pickup means, display of good images is realized. A detecting apparatus that enables lymph nodes to be detected readily is thereby realized. Such a detecting apparatus is especially useful for detecting the above-mentioned sentinel lymph node.

Here, the image pickup means is preferably arranged as being integral with the excitation light source. By providing such an arrangement in which the excitation light source and the image pickup means are disposed integrally, an apparatus that is simple in apparatus arrangement and easy to handle is realized. Also, with such an arrangement, the device can be made compact and inexpensive.

The optical filter preferably transmits the fluorescence image and transmits, at a predetermined light intensity, a reflection image from the living body observation portion illuminated by the excitation light. An observation image, in which the fluorescence image and the reflection image are overlapped, can thereby be obtained and ascertainment of the position of the lymph node in the living body observation portion is facilitated.

The image displaying means is preferably mountable onto a head portion of an observer. The need to hold the lymph node detecting apparatus by a hand during observation is thereby eliminated and the degree of freedom of tasks besides observation can be increased.

An image recording means for recording the observation image adjusted by the adjusting means may furthermore be equipped. Observation images during observation can thereby be recorded.

The lymph node detecting apparatus may furthermore be equipped with a light guide means for guiding the excitation light from the excitation light source to the living body observation portion, and an image guide means for guiding the fluorescence image from the living body observation portion to the image pickup means. In this case, the lymph node detecting apparatus is arranged as an endoscopic apparatus. The portion of a living body that is to be incised can thereby be made small. Also, image pickup can be performed close to a lymph node to enable the lymph node to be detected at higher precision.

Effects of the Invention

By this invention, a lymph node detecting apparatus that is simple in apparatus arrangement, is easy to handle, and displays good images can be realized.

BRIEF DESCRIPTION OF THE DRAWINGS

FIG. 4 shows schematic diagrams of (a) a fluorescence image, (b) a normal image, and (c) an observation image in which the images are overlapped, of a living body observation portion.

FIG. 6 shows graphs relating to luminance and contrast adjustments of an observation image by the adjusting device.

FIG. 7 shows photographs of examples of luminance and contrast adjustments of an observation image by the adjusting device.

DESCRIPTION OF SYMBOLS

Figure 1:
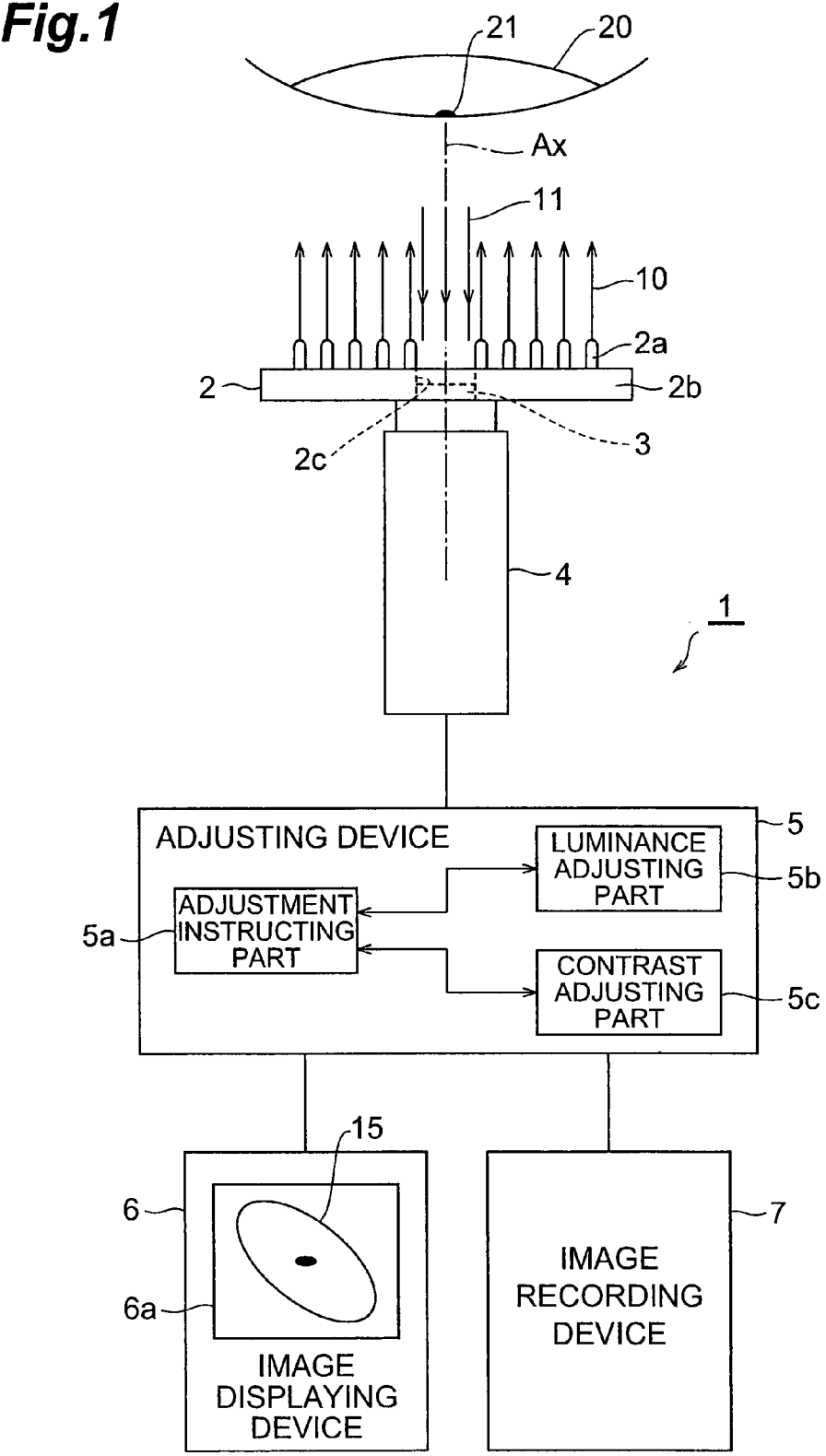
FIG. 1 is an arrangement diagram of a first embodiment of a sentinel lymph node detecting apparatus.

1—sentinel lymph node detecting apparatus, 2—excitation light source unit, 2a—excitation light source, 2b—supporting plate, 2c—opening, 3—optical filter, 4—image pickup device, 5—adjusting device, 5a—adjustment instructing part, 5b—luminance adjusting part, 5c—contrast adjusting part, 6—image displaying device, 6a—display part, 7—image recording device, 10—excitation light, 11—fluorescence image, 15—adjusted observation image, 20—living body observation portion, 21—sentinel lymph node.

BEST MODES FOR CARRYING OUT THE INVENTION

Preferred embodiments of a lymph node detecting apparatus according to this invention shall now be described in detail along with the drawings. In the description of the drawings, elements that are the same are provided with the same symbol and overlapping description shall be omitted. The dimensional proportions in the drawings do not necessarily match those of the description.

Figure 2:
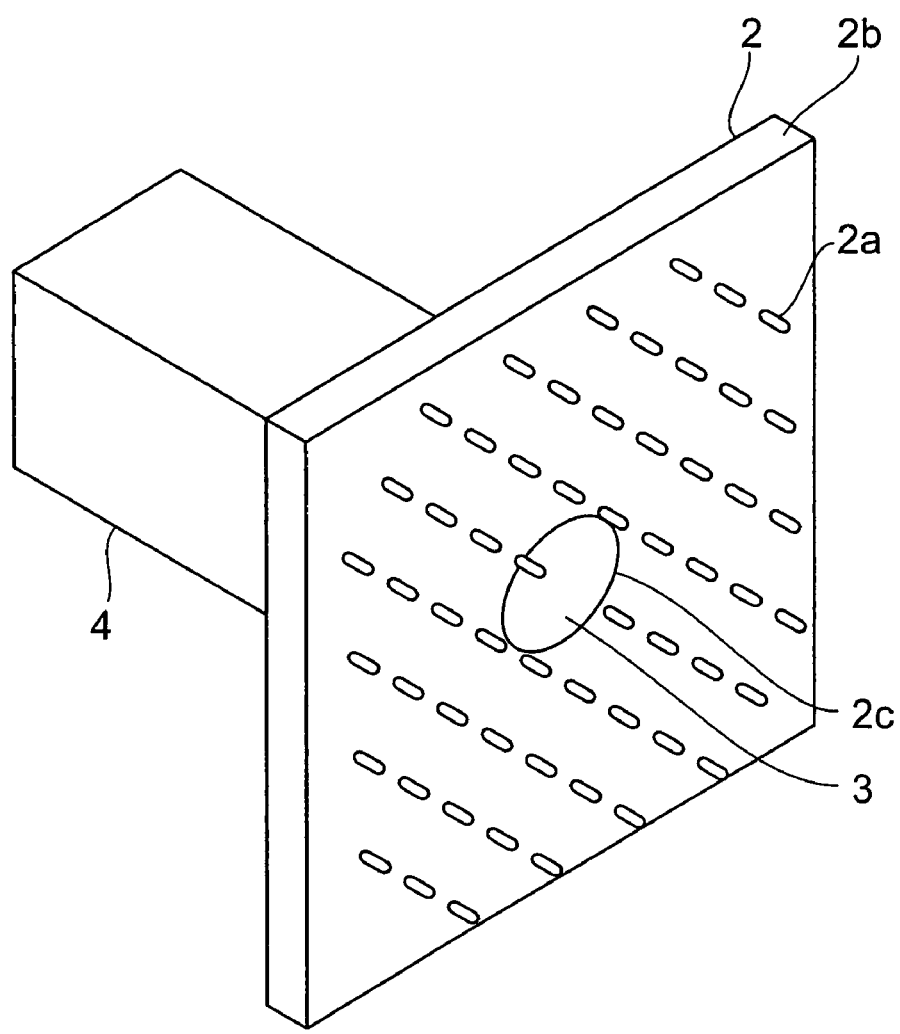
FIG. 2 is a perspective view of an arrangement of an excitation light source unit and an image pickup device used in the detecting apparatus shown in FIG. 1.

FIG. 1 is an arrangement diagram of a first embodiment of a sentinel lymph node detecting apparatus that is a lymph node detecting apparatus according to this invention. FIG. 2 is a perspective view of an arrangement of an excitation light source unit and an image pickup device used in the detecting apparatus shown in FIG. 1. The arrangement of the sentinel lymph node detecting apparatus of the embodiment shall now be described with reference to FIGS. 1 and 2.

With this sentinel lymph node detecting apparatus 1, an excitation light 10 of a predetermined wavelength is illuminated onto a living body observation portion 20 of a human body or other living body that includes a sentinel lymph node 21, and the sentinel lymph node is detected by observation of an image (fluorescence image 11) due to fluorescence emitted from living body observation portion 20. In the detection of the sentinel lymph node using this detecting apparatus 1, a fluorescent dye is injected close to a tumor inside living body observation portion 20 in advance. The fluorescence from the fluorescent dye that accumulates in the sentinel lymph node is then observed to detect the lymph node. The fluorescent dye used is selected suitably in consideration of the specific arrangement of detecting apparatus 1, etc., and as an example of such a fluorescent dye, indocyanine green can be cited.

Detecting apparatus 1, shown in FIG. 1, includes an excitation light source unit 2, an optical filter 3, an image pickup device 4, an adjusting device 5, and an image displaying device 6. Excitation light source unit 2 has a plurality of excitation light sources 2a and a supporting plate 2b, on one surface of which excitation light sources 2a are installed. Each of the plurality of excitation light sources 2a is a light source that emits, as the excitation light, light of the same wavelength and is used to illuminate excitation light 10 onto living body observation portion 20 that includes sentinel lymph node 21. Also, as shown in FIG. 2, excitation light sources 2a are arrayed two-dimensionally with a central axis Ax of excitation light source unit 2, which is an optical axis of detecting apparatus 1, as a symmetry axis.

As excitation light source 2a, a laser diode (LD) or a light emitting diode (LED) is preferably used. The wavelength of excitation light 10 supplied from excitation light source 2a is selected, based on the light absorbing characteristics, etc., of the fluorescent dye used for observation, to be a wavelength that can excite the fluorescent dye. For example, if the above-mentioned indocyanine green is used as the fluorescent dye, the light absorption band thereof is in the near-infrared wavelength band, and thus, a wavelength (such as a wavelength of 730 nm) within this wavelength band is selected and used as suited.

Supporting plate 2b is provided with an opening 2c at a central position that includes central axis Ax. This opening 2c lets fluorescence image 11, which is generated from living body observation portion 20 and enters from the front side of excitation light source unit 2, to pass through to the rear. The above-mentioned plurality of excitation light sources 2a are arrayed two-dimensionally so as to surround opening 2c. With such an arrangement, to prevent the intensity distribution of excitation light 10 that is illuminated toward living body observation portion 20 from being weak at the center due to the influence of opening 2c, the optical axes of excitation light sources 2a near opening 2c are preferably inclined toward central axis Ax.

Inside opening 2c of supporting plate 2b is installed optical filter 3, which, of the light from living body observation portion 20 that is to be the object of observation, transmits light of the wavelength band of fluorescence image 11 generated from living body observation portion 20. As optical filter 3, that having transmittance characteristics of cutting reflected light resulting from the reflection of excitation light 10 by living body observation portion 20 and other light of wavelengths besides fluorescence image 11, is preferably used.

Image pickup device 4 is installed at the rear of excitation light source unit 2. In the present embodiment, image pickup device 4 is disposed integrally with excitation light source unit 2 with optical axis Ax being matched. Fluorescence image 11, generated from the fluorescent dye in living body observation portion 20 that is excited by excitation light 10 illuminated from excitation light source 2a, thus reaches image pickup device 4 upon being transmitted through opening 2c of supporting plate 2b and optical filter 3. Image pickup device 4 picks up the incident fluorescence image 11 and outputs an obtained observation image as image data.

As image pickup device 4, for example, a CCD camera that can acquire a two-dimensional image is used. In particular, an image pickup device that can pick up light of the wavelength band of fluorescence image 11 (normally a near-infrared wavelength band, since a fluorescence image of approximately 800 nm is subject to detection) at high sensitivity is preferably used as image pickup device 4. To the plurality of excitation light sources 2a and image pickup device 4, an excitation light source power supply and an image pickup device power supply are respectively connected as necessary. However, the power supplies, etc., are omitted from illustration in FIG. 1. As these devices, those that are battery-driven may be used.

Adjusting device 5 is provided for the observation image output from image pickup device 4. This adjusting device 5 is an adjusting means for automatically or manually adjusting the image data of the observation image output from image pickup device 4. Adjusting device 5 in the present embodiment has a luminance adjusting part 5b and a contrast adjusting part 5c that perform adjustments of luminance and contrast, respectively, on the observation image from image pickup device 4. The conditions of adjustment of the observation image in adjusting parts 5b and 5c are instructed from an adjustment instructing part 5a. Adjustment instructing part 5a sets the adjustment conditions of the observation image automatically or according to inputs from an observer. However, if the adjustment conditions are fixed, such an adjustment instructing part 5a does not have to be provided. For transmission of the image data from image pickup device 4 to adjusting device 5, a wired or a wireless transmission method may be used.

Image displaying device 6 and image recording device 7 are connected to adjusting device 5. As an image for detecting sentinel lymph node 21, image displaying device 6 displays observation image 15, adjusted at adjusting device 5, on a display part 6a thereof. As this image displaying device 6, for example, a CRT monitor, a liquid crystal display mounted to the CCD camera that is image pickup device 4, etc., may be used. Image recording device 7 is a recording means for recording the data of the observation image adjusted at adjusting device 5. As this image recording device 7, for example, a videotape recorder that records the observation image onto a videotape that is a recording medium may be used.

A method for detecting a sentinel lymph node using sentinel lymph node detecting apparatus 1 shown in FIG. 1 shall now be described. First, the fluorescent dye, indocyanine green is injected close to a tumor. After the elapse of a predetermined time, the indocyanine green reaches sentinel lymph node 21 due to lymph flow. When excitation light 10 of the predetermined wavelength (for example, a wavelength of 730 nm) is then illuminated by excitation light source unit 2 onto living body observation portion 20 that includes sentinel lymph node 21, fluorescence image 11 of the near-infrared wavelength band is generated from living body observation portion 20 by the indocyanine green. Here, fluorescence image 11 is transmitted through while the reflected light from living body observation portion 20, illuminated by excitation light 10, is cut by optical filter 3.

Fluorescence image 11, transmitted through optical filter 3, is then picked up by the CCD camera that is image pickup device 4 and the data of the observation image is output from the CCD camera to adjusting device 5. Adjusting device 5 performs luminance and contrast adjustments on the observation image from image pickup device 4. Adjusted observation image 15, used for detecting the sentinel lymph node, is thus generated. By this image 15 being displayed on display part 6a of image displaying device 6, easy detection of sentinel lymph node 21 is realized. Image 15 is also recorded as necessary into the recording medium at image recording device 7.

The effects of sentinel lymph node detecting apparatus 1 according to the above-described embodiment shall now be described.

Detecting apparatus 1, shown in FIG. 1, has the arrangement where excitation light source unit 2, having excitation light sources 2a that illuminate excitation light 10 onto living body observation portion 20, and image pickup device 4, that picks up fluorescence image 11, are disposed integrally. Matching of the optical axes of excitation light source unit 2 and image pickup device 4 and other installation adjustment work are thus made unnecessary. Also, with this arrangement, there is no need to move excitation light source unit 2 and image pickup device 4 separately in moving detecting apparatus 1. Detecting apparatus 1 of a simple apparatus arrangement and easy handling is thus realized.

Also, the observation image acquired at image pickup device 4 is not displayed as it is on image displaying device 6, but the luminance and the contrast of the observation image are adjusted by means of adjusting device 5 and the adjusted observation image 15 is used as the image for detecting the sentinel lymph node. Display of a good image of living body observation portion 20 is thereby realized. By the above arrangement, detecting apparatus 1 that enables sentinel lymph node 21 to be detected readily is realized. Also, with this arrangement, the apparatus can be made compact and inexpensive. In regard to the positioning of adjusting device 5, it is preferably disposed close to or inside image pickup device 4.

Also, with excitation light source unit 2, shown in FIGS. 1 and 2, by two-dimensional arraying of the plurality of excitation light sources 2a, excitation light 10 can be illuminated uniformly across a predetermined range onto living body observation portion 20. Excitation light source 2a preferably has a function for adjusting the light intensity thereof. Also, optical filter 3 is preferably installed in front of a lens of image pickup device 4 or within image pickup device 4.

Figure 3:
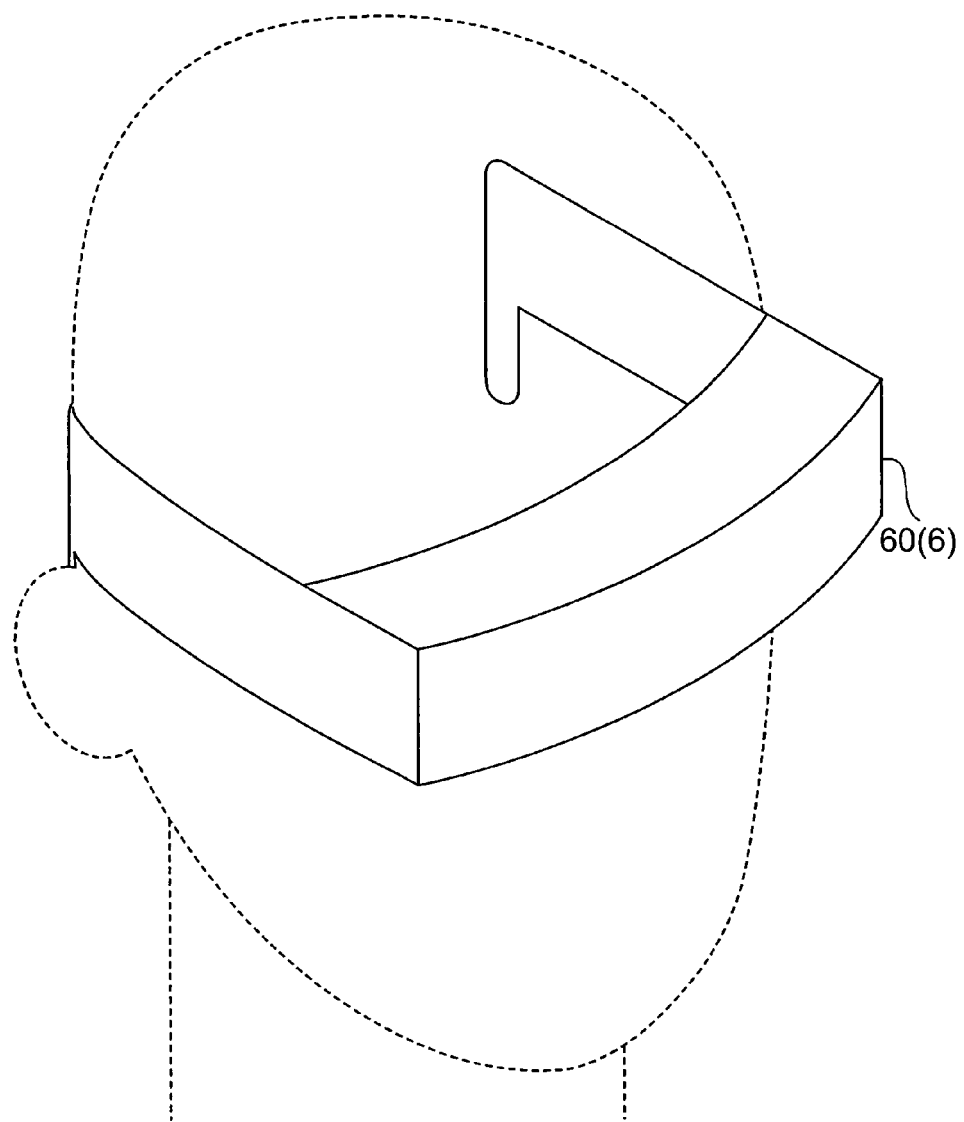
FIG. 3 is a perspective view of an example of an image displaying device.

Adjusting device 5, image displaying device 6, and image recording device 7 may be set up separately from or integrally with excitation light source unit 2 and image pickup device 4. As image displaying device 6, an arrangement (such as a goggle type or glasses type arrangement) that can be mounted onto a head portion of the observer as in the case of an image displaying device 60 shown in FIG. 3 is preferably used. The need to move or hold image displaying device 6, etc., with a hand during observation is thereby eliminated and the degree of freedom of work besides observation can be increased. In this case, the excitation light sources, the image pickup device, the adjusting device, and other components besides image displaying device 6 may be arranged to be integrally mounted along with the image displaying device.

Also, with the present embodiment, image recording device 7 is provided for the adjusted observation image from adjusting device 5. The observation image during observation can thereby be recorded. However, such an image recording device 7 does not have to be provided if it is unnecessary.

Optical filter 3, which selectively transmits fluorescence image 11 from among the light from living body observation portion 20, may transmit, at a predetermined light intensity, a reflection image from living body observation portion 20 illuminated by excitation light 10. As schematically shown in FIG. 4, an observation image, such as shown in FIG. 4(c), in which a fluorescence picture image, such as shown in FIG.

4(a) that corresponds to a fluorescence image, and a normal picture image, such as shown in FIG. 4(b) that corresponds to a reflection image, are overlapped, can thereby be obtained. The ascertainment of the position of sentinel lymph node 21 in living body observation portion 20 can thereby be facilitated.

When such an optical filter that transmits the reflection image (normal image) of the excitation light from living body observation portion 20 at a predetermined intensity is used, the reflection image is preferably transmitted at a light intensity no more than the fluorescence intensity of the fluorescence image, and especially in order to clearly distinguish fluorescence image 11, the reflection image is preferably transmitted at an intensity of no more than 10% and preferably approximately 10% of the fluorescence image.

Figure 5:
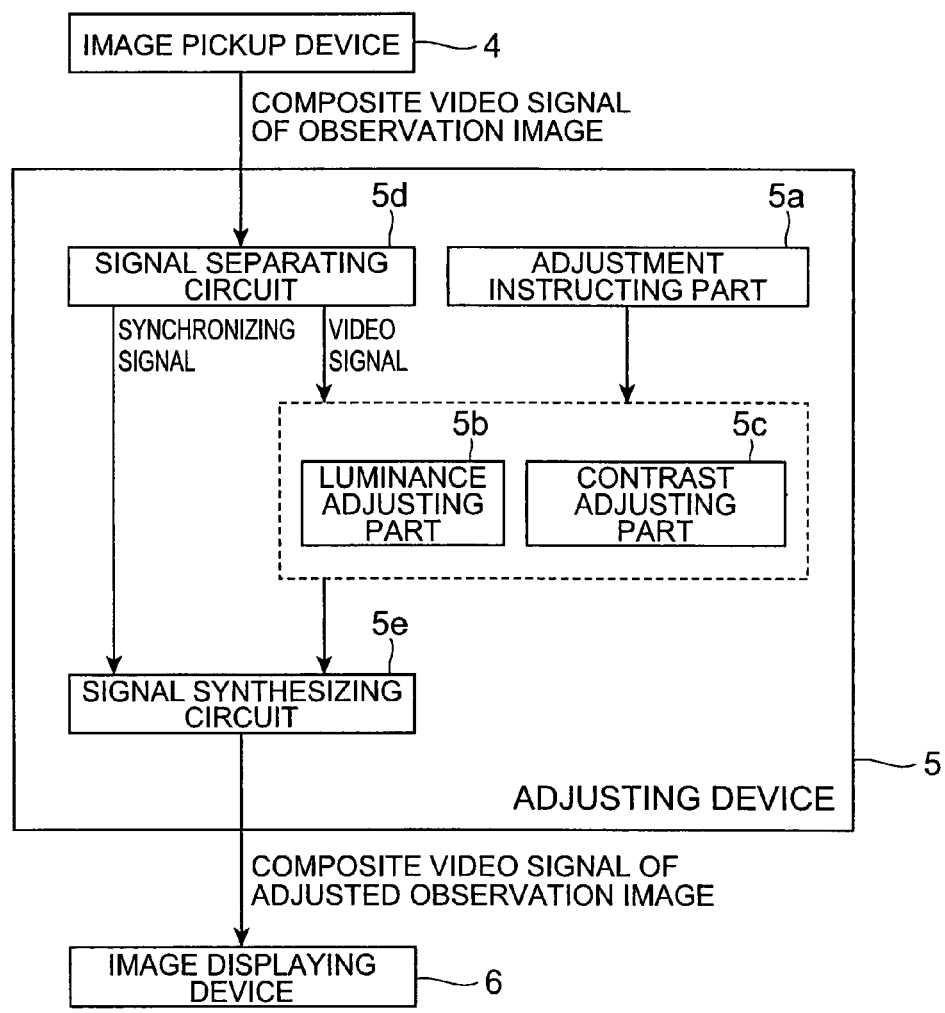
FIG. 5 is a block diagram of an arrangement example of an adjusting device used in the detecting apparatus of FIG. 1.

The arrangement of adjusting device 5 and the adjustments of the luminance and the contrast of the observation image shall now be described with a specific example. FIG. 5 is a block diagram of an arrangement example of the adjusting device used in the detecting apparatus shown in FIG. 1.

With this example, adjusting device 5 has, in addition to adjustment instructing part 5a, luminance adjusting part 5b, and contrast adjusting part 5c mentioned above with FIG. 1, a signal separating circuit 5d and a signal synthesizing circuit 5e. Normally, a composite video signal, made up of a video signal and a synchronizing signal, is output as the image data from image pickup device 4 that acquires the two-dimensional image. The composite video signal of the observation image that is input into adjusting device 5 from image pickup device 4 is separated into the synchronizing signal and the video signal at signal separating circuit 5d, and of these signals, the video signal is input into luminance adjusting part 5b and contrast adjusting part 5c. Adjusting parts 5b and 5c perform luminance and contrast (gain and offset) adjustments on the video signal according to adjustment conditions instructed from adjustment instructing part 5a. The video signal adjusted at adjusting parts 5b and 5c and the synchronizing signal are then synthesized again by signal synthesizing circuit 5e and output as the composite video signal of the adjusted observation image to image displaying device 6.

Such adjustments of the observation image are especially useful in the case where the optical filter, which transmits, in addition to the fluorescence image (fluorescence picture image), the reflection image (normal picture image) from the living body observation portion at the predetermined intensity, is used as described above. FIG. 6 shows graphs relating to luminance and contrast adjustments of an observation image by the adjusting device. FIG. 7 shows photographs of examples of luminance and contrast adjustments of an observation image by the adjusting device.

When the optical filter, which transmits a portion of the reflection image, is used as described above, the normal picture image and the fluorescence picture image are mixed in the video signal as shown in FIG. 6(a). By performing an adjustment of enhancing the contrast on this video signal as shown in FIGS. 6(b) and 7(a), an image in which the lymph node appears clearly can be obtained. Also, by performing an adjustment of enhancing the luminance as shown in FIGS. 6(c) and 7(b), the position of the lymph node in the living body observation portion can be ascertained clearly from the image in which the normal picture image and the fluorescence picture image are overlapped. By thus performing luminance and contrast adjustments on an observation image, a good observation image can be obtained. As the specific adjusting method, suitable settings may be made according to the purpose as in the examples of adjusting the luminance or contrast. In general, adjusting device 5 is arranged to adjust at least one of the luminance and the contrast of the observation image.

The lymph node detecting apparatus according to this invention shall now be described further.

Figure 8:
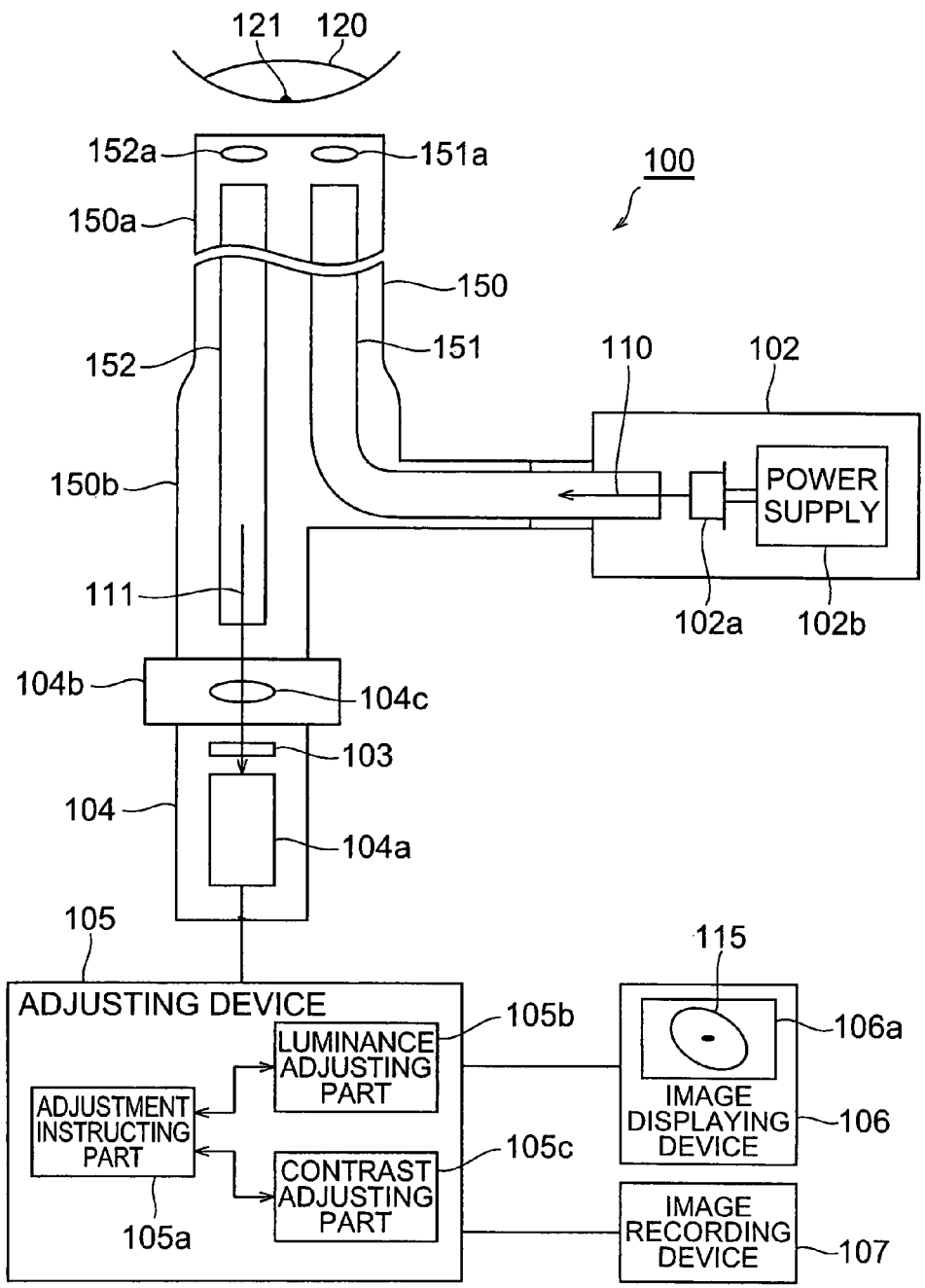
FIG. 8 is an arrangement diagram of an endoscopic apparatus that is a second embodiment of the lymph node detecting apparatus.

FIG. 8 is an arrangement diagram of an endoscopic apparatus that is a second embodiment of the lymph node detecting apparatus according to this invention.

With this endoscopic apparatus 100, an excitation light 110 of a predetermined wavelength is illuminated onto a living body observation portion 120 of a living body that includes a sentinel lymph node or other lymph node 121, and the lymph node is detected by observation of an image (fluorescence image 111) due to fluorescence emitted from living body observation portion 120.

Endoscopic apparatus 100, shown in FIG. 8, includes an excitation light source unit 102, an optical filter 103, an image pickup device unit 104, an adjusting device 105, an image displaying device 106, and a fiberscope 150. Fiberscope 150 includes a long, thin, flexible inserted portion 150a that is inserted into a body and used to observe living body observation portion 120, and a manipulating portion 150b that is disposed at a base portion with respect to inserted portion 150a.

Fiberscope 150 is provided with a light guide optical fiber 151, which is a light guide means that guides excitation light 110 from excitation light source unit 102 to living body observation portion 120, and an image guide optical fiber 152, which is an image guide means that guides the fluorescence image from living body observation portion 120 to image pickup device unit 104. Also, lenses 151a and 152a are disposed at respective end portions at the inserted portion 150a side of optical fibers 151 and 152.

Excitation light source unit 102 is connected to an end portion at the manipulating portion 150b side of light guide optical fiber 151. This excitation light source unit 102 has a single excitation light source 102a and an excitation light source power supply 102b. Excitation light source 102a is arranged from a light source that emits light of the predetermined wavelength as the excitation light, and is used to illuminate excitation light 110 onto living body observation portion 120 that includes lymph node 121. The same description as that provided in relation to FIG. 1 applies in regard to the wavelength, etc., of excitation light 110.

Image pickup device unit 104 is connected to an end portion at the manipulating portion 150b side of image guide optical fiber 152. This image pickup device unit 104 has optical filter 103 that transmits light of the wavelength band of fluorescence image 111 generated from living body observation portion 120, and an image pickup device 104a that picks up fluorescence image 111 that has been transmitted through optical filter 103. Also, an image forming optical system 104b, including an image forming lens 104c, is disposed between optical fiber 152 and image pickup device unit 104.

Adjusting device 105 is provided for an observation image output from image pickup device 104a. As with adjusting device 5 shown in FIG. 1, adjusting device 105 of the present embodiment has a luminance adjusting part 105b and a contrast adjusting part 105c that respectively perform luminance adjustment and contrast adjustment on the observation image from image pickup device 104a. The conditions of the adjustments of the observation image at adjusting parts 105b and 105c are instructed from an adjustment instructing part 105a.

Image displaying device 106 and an image recording device 107 are connected to adjusting device 105. Image displaying device 106 displays observation image 115, adjusted at adjusting device 105, on a display part 106*a* as an image for detecting sentinel lymph node 121. Image recording device 107 is a recording means for recording the data of the observation image adjusted at adjusting device 105.

As with detecting apparatus 1, shown in FIG. 1, with endoscopic apparatus 100 that is the lymph node detecting apparatus shown in FIG. 8, the observation image acquired by image pickup device 104*a* is not displayed as it is on image displaying device 106 but the luminance and the contrast of the observation image are adjusted by means of adjusting device 105, and the adjusted observation image 115 is used as the image for detecting the lymph node. The display of a good image of living body observation portion 120 is thereby realized. By the above arrangement, endoscopic apparatus 100 that enables lymph node 121 to be detected readily is realized.

Also, by applying the above arrangement to an endoscopic apparatus, the portion of a living body that is to be incised can be made small. Also, image pickup can be performed close to a lymph node to enable the lymph node to be detected at higher precision.

The sentinel lymph node detecting apparatus according to this invention is not restricted to the above-described embodiments and arrangement examples, and various modifications are possible. For example, though in regard to the excitation light source that illuminates excitation light onto a living body observation portion, excitation light source unit 2, having a plurality of excitation light sources 2*a*, was used in the above-described embodiment, a single excitation light source may be used instead as in the embodiment shown in FIG. 8. In regard to the image data output from the image pickup device, if noise in the image data is a problem in the case of a live moving image (30 Hz), etc., a recursive filter or other filtering method may be employed to reduce the noise and obtain a clearer fluorescence image. Also, the detecting apparatus of the above arrangement is not restricted to a sentinel lymph node detecting apparatus and can be applied generally as a lymph node detecting apparatus.

In regard to the fluorescent dye used to observe the sentinel lymph node, though a water-soluble fluorescent dye is generally used, since a fluorescent dye, with which a fluorescent dye is dissolved in physiological saline, etc., is generally small in molecular weight, it may not stay in the lymph node that is reached first and may reach a second or a third lymph node. In this case, by using a quantum dot of a diameter of several dozen nm that emits near-infrared fluorescence or a fluorescent tracer, in which a fluorescent reagent is bound to a metal colloid or to latex beads, improvement of the precision of identification of the sentinel lymph node position can be anticipated.

INDUSTRIAL APPLICABILITY

This invention can be used as a lymph node detecting apparatus that is simple in apparatus arrangement, is easy to handle, and enables good images to be displayed.

The invention claimed is:

1. A lymph node detecting apparatus comprising:
    an excitation light source unit, illuminating excitation light onto a living body observation portion that includes a lymph node near a tumor into which a fluorescent dye that emits fluorescence of a predetermined wavelength has been injected in advance;
    an optical filter, transmitting a fluorescence image generated from the living body observation portion;
    an image pickup device, picking up the fluorescence image transmitted through the optical filter;
    an adjusting means, adjusting at least one of a luminance and a contrast of an observation image output from the image pickup device; and
    an image displaying means; displaying the observation image, adjusted by the adjusting means, as an image for detecting the lymph node, wherein
    the optical filter transmits simultaneously, in addition to the fluorescence image, at a predetermined light intensity, a reflection image from the living body observation portion illuminated by the excitation light, and
    the observation image, in which a fluorescence picture image that corresponds to the fluorescence image and a normal picture image that corresponds to the reflection image of the excitation light are overlapped, is obtained by the image pickup device,
    the excitation light source unit has a plurality of excitation light sources and a supporting plate, on one surface of which the plurality of excitation light sources are installed,
    each of the plurality of excitation light sources is a light source that emits, as the excitation light, light of the same wavelength, and
    the plurality of excitation light sources are arrayed two-dimensionally with a central axis of the excitation light source unit, which is matched with an optical axis of the image pickup device, as a symmetry axis.

2. The lymph node detecting apparatus according to claim 1, wherein the image pickup device is integral with the excitation light source unit.

3. The lymph node detecting apparatus according to claim 1, wherein the image displaying means is mountable onto a head portion of an observer.

4. The lymph node detecting apparatus according to claim 1, further comprising an image recording means, recording the observation image adjusted by the adjusting means.

5. The lymph node detecting apparatus according to claim 1, further comprising: a light guide means for guiding the excitation light from the excitation light source unit to the living body observation portion; and an image guide means for guiding the fluorescence image from the living body observation portion to the image pickup device; and being arranged as an endoscopic apparatus.

6. The lymph node detecting apparatus according to claim 1, wherein the optical filter transmits the reflection image at the light intensity no more than the fluorescence intensity of the fluorescence image.

7. The lymph node detecting apparatus according to claim 1, wherein the optical filter transmits the reflection image at the light intensity of no more than 10% of the fluorescence intensity of the fluorescence image.

* * * * *